United States Patent
Wu

(10) Patent No.: US 6,632,431 B2
(45) Date of Patent: Oct. 14, 2003

(54) **ANTI-IDIOTYPIC ANTIBODY AGAINST FIMH ADHESION OF UROPATHOGENIC TYPE I-FIMBRIATED *ESCHERICHIA COLI*, COMPOSITIONS CONTAINING SAME AND METHOD FOR USING SAME**

(75) Inventor: Xue-Ru Wu, Staten Island, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 09/852,283

(22) Filed: May 10, 2001

(65) Prior Publication Data

US 2002/0028200 A1 Mar. 7, 2002

Related U.S. Application Data

(60) Provisional application No. 60/204,572, filed on May 16, 2000.

(51) Int. Cl.$^7$ .............................. A61K 39/395
(52) U.S. Cl. ................. 424/131.1; 424/141.1; 424/422; 424/423; 424/426; 424/184.1; 424/204.1; 424/206.1; 424/259.1; 424/274.1; 424/239.1; 530/387.1; 530/387.2; 435/7.1
(58) Field of Search ........................ 435/7.1; 424/141.1, 424/131.1, 92, 88, 85, 87, 422, 423, 426, 184.1, 204.1, 206.1, 289.1, 274.1, 239.1; 530/387.1, 387.2

(56) References Cited

U.S. PATENT DOCUMENTS

| | | | | |
|---|---|---|---|---|
| 4,725,435 A | * | 2/1988 | Brinton, Jr. et al. | 424/92 |
| 4,801,690 A | * | 1/1989 | Brinton, Jr. et al. | 530/396 |
| 5,538,733 A | * | 7/1996 | Emery et al. | 424/422 |
| 5,656,271 A | * | 8/1997 | MacDonald et al. | 424/131.1 |
| 5,840,297 A | * | 11/1998 | MacDonald et al. | 424/131.1 |
| 6,268,171 B1 | * | 7/2001 | Meyer et al. | 435/69.1 |
| 6,290,959 B1 | * | 9/2001 | Wu et al. | 424/150.1 |
| 6,368,599 B1 | * | 4/2002 | Langermann et al. | 424/184.1 |

OTHER PUBLICATIONS

Paque, RE et al, Infection and Immunity, Mar. 1990, vol. 58(3), pp. 680–686, Polyclonal anti–idiotypic antibodies exhibit antigenic mimicry if limited type 1 fimbrial proteins of *Escherichia coli*.*
Stein, KE et al, Journal of Experimental medicine, Oct. 1, 1984, vol. 160(4), pp. 1001–1011.*
Khan, AS et al, Infection and Immunity, Jun. 200, vol. 68(6), pp. 3541–3547 (abstract only).*
Mett, H et al, Infection and Immunity, Jun. 1983, vol. 40(3), pp. 862–868, Fimbria–specific antibodies detach *Escherichia coli* from human cells.*
Abraham, SN et al, Infection and Immunity, vol. 48(3), pp. 625–628, Jun. 1985.*
Lund, B et al, Molecular Microbiology, vol. 2(2), pp. 255–263, Mar. 1988 (abstract only).*
Rudin, A et al, Infection and Immunity, vol. 64(11), pp. 4508–4513, Nov. 1996.*
Sokurenko, E.V. et al, (1998), PNAS, USA, vol. 95, pp. 8922–8926, Jul. 1998.*
Sokurenko, EV et al (1995), Journal of Bacteriology, vol. 177(13), pp. 3680–3686, Jul. 1995.*
Thankavel, K et al, (1997), J. Clin. Invest. vol. 100(5), pp. 1123–1136, Sep.*
Nicholes, A et al, Abstracts of the General Meeting of the American Society for Microbiology, vol. 94(00, May 23–27 1994, p. 118 (abstract).*
Sokurenko, E et al, Abstracts of the General Meeting of the American Society for Microbiology, vol. 93(0), p. 113, May 16–20, 1993 (abstract only).*
Sokurenko, E et al Abstracts of the General Meeting of the American Society of Microbiology, vol. 94(0), p. 118, 1994.*
Burlein, JE et al, Abstracts of the General Meeting of the American Society of Microbiology, vol. 97(0), p. 76, May 4–8, 1997 (abstract only).*
Langermann et al., Prevention of mucosal *Escherichia coli* infection by FimH adhesin–based systemic vaccination, *Science*, 276:607–611 (1997).
Sokurenko et al., FimH family of type 1 fimbrial adhesions: functional heterogeneity due to minor sequence variations among fimH genes, *Journal of Bacterbiology*, 176(3)748–755 (1994).
Sokurenko et al., Quantitative differences in adhesiveness of type 1 fibriated *Escherichia coli* due to structural differences in finH genes, *Journal of Bacteriology*, 177(13)3680–3686 (1995).
Poskitt et al., Short reviews internal image (Ab2$\beta$) anti–idiotype vaccines. Theoretical and practical aspects, *Vaccine*, 9:792–796 (1991).
Shoenfeld et al., Anti–idiotypes and their application under autoimmune, neoplastic, and infectious conditions, *Int Arch Allergy Immunol*, 105:211–223 (1994).
Service, New vaccines may ward off urinary tract infections, *Science*, 276:533 (1997).
Sokurenko et al., Diversity of the *Escherichia coli* type 1 fimbrial lectin. Differential binding to mannosides and uroepithelial cells, *J. Biol. Chem*, 272(28):17880–17886 (1997).

(List continued on next page.)

*Primary Examiner*—Lynette R. F. Smith
*Assistant Examiner*—Ginny Allen Portner
(74) *Attorney, Agent, or Firm*—Browdy and Neimark

(57) ABSTRACT

The present invention relates to an anti-idiotypic antibody or antigen-binding fragment against FimH adhesin of uropathogenic Type I-fimbriated *Escherichia coli* and an immunizing composition containing such an anti-idiotypic antibody or antigen-binding fragment thereof as an active immunizing component. The present invention also relates to a method for stimulating and enhancing the production of antibodies which recognize and bind to FimH of uropathogenic Type-I-fimbriated *Escherichia coli*, but not to FimH of non-uropathogenic Type I-fimbriated *Escherichia coli*.

4 Claims, No Drawings

OTHER PUBLICATIONS

Klemm et al., Three fim genes required for the regulation of length and mediation of adhesion of *Escherichia coli* type 1 fimbriae, *Mol Gen Genet*, 208:439–445 (1987).

Hultgren et al., Pilus and nonpilus bacterial adhesions: assembly and function in cell recognition, *Cell*, 73:887–901 (1993).

Thankavel et al., Localization of a domain in the FimH adhesin of *Escherichia coli* type 1 fimbriae capable of receptor recognition and use of a domain–specific antibody to confer protection against experimental urinary tract infection, *J. Clin. Invest.*, 100(5)1123–1136 (1997).

Jones et al., FimH adhesin of type 1 pili is assembled into a fibrillar tip structure in the *Enterobacteriaceae*, *Proc. Natl. Acad. Sci. USA*, 92:2081–2085 (1995).

Abrahan et al., Identification of two ancillary subunits of *Escherichia coli* type 1 fimbriae by using antibodies against synthetic oligopeptides of fim gene products, *Journal of Bacteriology*, 169:5530–5536 (1987).

Jones et al., FimC is a periplasmic papD–like chaperone that directs assembly of type 111 pili in bacteria, *Proc. Natl. Acad. Sci. USA*, 90:8397–8401 (1993).

Friboulet et al., Monoclonal anti–idiotypic antibodies as functional internal images of enzyme active sites: production of a catalytic antibody with a cholinesterase activity, *Proc Natl Acad Sci USA*, 90(19):8876–8880 (1993).

Chakraborty et al., Induction of antitumor immunity by an anti–idiotype antibody mimicking carcinoembyonic antigen, *Cancer Res*, 57(4)728–734 (1997).

Dalgleish et al., Anti–idiotypic antibodies as immunogens: idityp–based vaccines, *Vaccine*, 6(3)215–220 (1988).

Langermann et al., Vaccination with FimH adhesin protects cynomolgus monkeys from colonization and infection by uropathogenic *Escherichia coli, The Journal of Infectious Diseases*, 181:774–8 (2000).

Kennedy et al., Anti–idiotypic antibody vaccine for type B viral hepatitis in chimpanzees, *Science*, 232:220–223 (1986).

Hiernaux, Minireview idiotypic vaccines and infectious diseases, *Infection and Immunity*, 1407–1413 (1988).

Langermann et al., Prevention of mucosal *Escherichia coli* infection by FimH–adhensin–based systemic vaccination, *Science*, 276:607–611 (1997).

* cited by examiner

US 6,632,431 B2

ANTI-IDIOTYPIC ANTIBODY AGAINST FIMH ADHESION OF UROPATHOGENIC TYPE I-FIMBRIATED *ESCHERICHIA COLI*, COMPOSITIONS CONTAINING SAME AND METHOD FOR USING SAME

CROSS-REFERENCE TO RELATED APPLICATION

This application claims the benefit of priority from U.S. Provisional Application No. 60/204,572, filed May 16, 2000, the entire content of which is incorporated herein by reference.

BACKGROUND OF THE INVENTION

1. Field of Invention

The present invention relates to an anti-idiotypic antibody and a composition containing same, such as an immunizing composition.

2. Description of the Related Art

Urinary tract infection (UTI) is one of the most common infectious diseases that primarily affect women of all ages. Nearly as many as 50% of all women experience at least one infection in the urinary tract during their lifetimes. Although as prevalent as the common cold, UTI causes far more discomfort and sends 10 million people annually in the United States alone to seek medical attention. Approximately 1.5 million of these visits are diagnosed as pyelonephritis (kidney infection), which is often so serious that hospitalization is required. In addition, approximately 20% of women experience frequent infections (on the order of three to six per year) after the initial episode of UTI, resulting in additional morbidity and lost productivity. It is estimated that five billion healthcare dollars are spent each year to treat UTIs.

Over 85% of all UTIs are caused by the enterobacteria *Escherichia coli*, and an overwhelming majority of these *E. coli* bacteria express surface filamentous organelles called Type I fimbriae. Experimental and epidemiological studies have established that Type I fimbriae are the major virulence factor of uropathogenic *E. coli*, where these fimbriae function as an adhesive apparatus that allows *E. coli* to bind to the epithelial lining, urothelium, of the urinary tract. Such a binding between the invading *E. coli* and the host urothelial surface is a pivotal step in the establishment of *E. coli* colonization within the urinary tract.

Type I fimbriae are hairlike structures which emanate from the surface of *E. coli* and nearly all members of the Enterobacteriaceae family (Brinton, 1965). The major component of Type I fimbriae is repeating subunits of FimA arranged in a right-handed helix to form a filament approximately 1 $\mu$m in length and 7 nm in diameter with a central axial hole (Brinton, 1965). Along with FimA as the major subunit, the fimbrial filament also contains FimF, FimG and FimH as minor protein subunits (Maurer et al, 1987; Abraham et al, 1987; Russel et al, 1992). The minor protein subunit FimH is a mannan-binding adhesin that promotes adherence of Type I-fimbriated bacteria to mannose-containing glycoproteins on eukaryotic cell surfaces and represents a family of proteins which bind to various targets, including mannan and fibronectin (Abraham et al, 1987; Ofek et al, 1977; Sokurenko et al, 1994). Immune electron microscopy studies have revealed that FimH is strategically placed at the distal tips of Type I fimbriae where it appears to be complexed with FimG, forming a flexible fibrillum structure (Abraham et al, 1987 and 1988; Jones et al, 1995), and is also placed longitudinally at various intervals along the filament (Abraham, 1987 and 1988).

While prophylaxis with antibiotics offers quick relief against most UTIs, it is not free from serious drawbacks. For most patients suffering from uncomplicated UTIs, a three-day regimen of trimethoprim/sulfamethozole or a seven-day course of nitrofurandantoin usually stops the infection. However, for some patients, they soon develop side effects, such as vaginitis, gastrointestinal upset and rashes, from the antibiotic, conditions which then require further medical attention. One in five women who experience one infection will experience another infection within weeks. For these patients, a low dose but much longer course (six months to two years) of antibiotics is prescribed to reduce the frequency of reinfections. Although the efficacy of antibiotic prophylaxis for recurrent UTIs has been recently demonstrated, major problems persist in the areas of patient compliance, adverse effects of antibiotics, emergence of bacterial resistance, along with the associated costs of long-term medication. Recent studies show that antibiotic prophylaxis results in a dramatic change in the population of uropathogens reinfecting the host (Reid, 1997). Infections caused by these new strains are generally more difficult to control. Recurrent UTIs not only present a challenge to clinical management, but also significantly increase the risk of kidney involvement, such as pyelonephritis, and complicated UTIs that often require hospitalization and initial parenteral antibiotic therapy. In this situation, a newer generation of antibiotics (e.g., quinolones) or a combination of several antibiotics is usually indicated. However, resistance has been now reported even for these newer generation of antibiotics.

The prevalence of UTIs and the emergence of antibiotic-resistant microorganisms call for novel preventative and therapeutic strategies. One effective approach is the development of vaccines against causative agents of UTIs. The overwhelming majority of UTIs (>85%) are caused by *E. coli*, most of which are Type I-fimbriated. Type I fimbriae serve as an adhesive apparatus, via their tip FimH adhesins, for enabling the bacteria to attach to the urothelial surface.

Past efforts in developing a UTI vaccine have been met with limited success. For example, an injectable cocktail containing heat-killed uropathogenic *E. coli* called Urovac has been available in Europe since the 1980s. However, the efficacy of this vaccine is questionable as it provides limited protection against UTIs. Not only is the protection short-lived, but also the toxins in intact *E. coli* cause significant side effects, including painful inflammation around the injection sites. To circumvent these problems, a group in Wisconsin tested an alternative delivery method (vaginal suppository) using the same vaccine. Preliminary clinical trials have shown short-term protection against recurrence as UTI-prone patients are less prone to be reinfected. Again, the protection appears to be short-lived. The major drawback of using the entire *E. coli* as a vaccine also lies in the fact that the FimH adhesin, which is a minor protein in *E. coli*, is under-presented as an antigen and, thus, unlikely to elicit a sufficient immune response that would target the process of *E. coli* adherence to the urothelial surface.

A new strategy that was recently tested by a group in St. Louis utilizes recombinant FimH adhesin as a UTI vaccine (Langermann et al, 1997). Immunization of mice with this putative FimH vaccine reduced in vivo colonization of the bladder mucosa by more than 99% in a mouse cystitis model. Immunoglobulin G to FimH was detected in the urine of protected mice. These studies suggest that an anti-FimH approach can be effective in preventing urinary colonization by uropathogenic *E. coli* (Langermann et al, 1997; Service, 1997). However, there are two major limitations with this approach which, if unresolved, can prevent the FimH-based vaccine from clinical use. First, it is difficult to produce large amounts of FimH protein. FimH expressed alone in *E. coli* using the recombinant approach is easily degraded. When co-expressed with a chaperone protein (FimD), FimH is somewhat stabilized, but remains at a very low level (Langermann et al, 1997). This can limit the use of FimH as a vaccine. Second, the current putative FimH preparation does not discriminate FimH-carrying uropathogenic *E. coli* and FimH-carrying intestinal *E. coli*, the latter of which are beneficial flora. Host immune response targeted against FimH vaccine will likely suppress intestinal *E. coli*, which could lead to serious side effects (Service, 1997).

Idiotypes have been intensively studied following Jerne's immune network theory in 1974. One of his major proposals is the self-regulation of the immune system through a network of idiotype-anti-idiotype interactions (Jerne, 1974). It was suggested that the idiotopes on a single antibody molecule can mimic and be the "internal image" of any foreign or self epitope at the molecular level. Internal image determinants have been proposed for use in vaccines (Nisonoff et al, 1981). By means of Mab technology, a protective antibody (Ab1) to an epitope of interest on the pathogen can be produced. The particular antibody (Ab1) can be purified and subsequently used as an immunogen to elicit an anti-idiotypic antibody (Ab2) which may be an internal image of the original epitope on the pathogen. Thus, as predicted by the Jerne "network" theory (Jerne, 1974), immunization with an anti-idiotypic antibody (Ab2) that is directed against antigen combining sites of primary antibody (Ab1), may elicit a humoral immune response specific for the nominal antigen. The resulting anti-anti-idiotypic antibody (or Ab3) should react with the original primary antigen. If the primary antigen is an oligosaccharide (and, therefore, expected to give a T-cell independent immune response), the immunization with Ab2 (the protein equivalent) may elicit a T-cell dependent response.

All idiotypes of a single immunoglobulin molecule have been found to be located on the Fv (fragment variable) region by studies showing that the inhibition of binding of anti-idiotypic antibodies to the idiotype is the same between Fv and Fab. In general, anti-idiotypic antibodies are divided into three types Ab2α, Ab$_2$β and Ab$_2$ε. Only Ab$_2$β, which binds to the complementarity determining region (CDR), can be the internal image of the antigen and has been proposed to be paratropic and to mimic the molecular features of the original antigen (Nisonoff et al, 1981; Roitt, 1985). The occurrence of Ab2 displaying the internal image of the antigen must adhere to the following criteria: (1) binding onto Ab1 and to any other anti-nominal antigen antibodies from another species and lack of reactivity with Ab2 to other antibodies; (2) inhibition of the binding of Ab1 to the specific antigen, the nominal antigen; and (3) the ability to elicit the synthesis of Ab3 with anti-antigen specificity in animals without previous exposure to the antigen.

The important role of anti-idiotypic antibodies in vivo has been shown in numerous experiments. The administration of anti-idiotypic antibodies was found to elicit different effects, either suppression or enhancement of the responses to the specific idiotype (Kennedy, 1983). In autoimmunity, it certainly plays an important role. The pathology associated with many autoimmune diseases is most likely due to (at least in part) a direct idiotype-anti-idiotype interaction of the autoimmune antibodies with anti-idiotypic antibodies. Idiotypic specificity in a specific antibody was first characterized by demonstrating that specific hapten binding could inhibit idiotype recognition.

The best information for the exact molecular basis for the mimicking is presently obtained from the X-ray crystallography of the idiotype-anti-idiotype complex. The basis of molecular mimicry of the antibodies can be either local sequence homology to the original protein as in a reovirus system or, in most cases, identical conformations from entirely different amino acid sequences, as in the hemoglobin-myoglobin family of proteins. X-ray crystallography and sequence data in the later studies showed that identical, functional conformations can be assumed by proteins that differ by as many as 137 of 141 amino acids. The studies of the crystal structure of idiotype-anti-idiotope complex in the anti-lysozyme antibody and the anti-idiotope have demonstrated that a private idiotope consists of 13 amino acid residues, most from the complementarity determining regions (CDRs), but including three residues from the third framework region of its $V_L$ domain. Seven of these residues are common with the paratope of anti-lysozyme antibody, indicating a significant overlap between idiotope and antigen-combining site. Idiotype has been a unique tool in the characterization and the manipulation of the immune response since it was discovered as a clonal marker to follow B cell development, somatic mutation and fate of clones of B cells. Idiotypes have been used as a phenotypic marker for germ line V genes.

Anti-idiotypic antibodies, which bear the internal image of external pathogens, such as virus, bacteria or parasites, have been successfully used as surrogate antigens in vaccines (Hiernaux, 1988; Eichmann et al, 1987; Kennedy et al, 1983; Kennedy et al, 1986; McNamara et al, 1984; Schreiber et al, 1990; Schreiber et al, 1990; Stein et al, 1984; Westerink et al, 1988) to elicit a humoral immune response specific for the nominal antigen and are also being used in treating B cell lymphoma and autoimmune disease, such as encephalomyelitis. In addition, it has been shown that anti-idiotypic antibodies can induce T-cell responses in which either toxic T-cells or T-helper cells that recognize the original antigen are produced.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

It is an object of the present invention to solve the problems associated with UTI vaccines. In particular, the present invention overcomes the difficulties associated with a FimH-based UTI vaccine in obtaining large quantities of FimH adhesin and in being specific for uropathogenic Type I-fimbriated *E. coli* so as to avoid the adverse effects caused by elimination of beneficial intestinal *E. coli*.

The present invention provides an anti-idiotypic antibody or an antigen binding fragment thereof which mimics FimH adhesin and serves as a surrogate for FimH in generating a humoral immune response as well as possibly a cellular immune response. Thus, the present invention also provides an immunizing composition and a method for stimulating and enhancing the production of antibodies which recognize and bind to FimH adhesin of uropathogenic Type I-fimbriated *Escherichia coli* but not to FimH adhesin of non-uropathogenic Type I-fimbriated *Escherichia coli* by administering the immunizing composition to a subject.

DETAILED DESCRIPTION OF THE INVENTION

An effective approach that can overcome the limitations of FimH-based vaccines, as discussed above, is the anti-idiotypic antibody approach. This is based on the fact that the variable regions of anti-idiotypic antibodies mimic the antigenic determinants of the original antigen (Schoenfeld et al, 1994; Dalgleish et al, 1988; Poskitt et al, 1991). The major advantages of anti-idiotype-based vaccines are that unlimited amounts of vaccine (antibodies) can be produced and that the anti-idiotypic antibodies are highly immunogenic molecules. More importantly, the anti-idiotypic approach provides the opportunity for the generation of vaccines specific for uropathogenic *E. coli* FimH adhesins, but not for intestinal *E. coli* FimH adhesins, thus averting potentially serious side effects of FimH protein-based vaccines where the elicited immune response is also directed against beneficial *E. coli* flora in the intestines.

Studies by Hasty and colleagues reported that FimH adhesins are not homogeneous, but exhibit phenotypic variations (Sokurenko et al, 1994, 1995 and 1997). Although FimH adhesins of *E. coli*, regardless of whether they are fecal or UTI isolates, can all bind to mannoses, two discrete phenotypes are observed. *E. coli* that were isolated from UTI patients have a much higher affinity for monomannosyl sugar groups of different substrates than for trimannosyl groups. In contrast, *E. coli* isolated from fecal flora bind to trimannosyl sugar groups much more strongly than to monomannosyl groups (Sokurenko et al, 1997). Such a selective binding of different FimH phenotypes to different substrates has been confirmed on uroplakin receptors found on the urothelium, as UTI isolates bind to uroplakins Ia and Ib much more strongly than the fecal isolates. Recent work by Sokurenko and Hasty further demonstrated that the different FimH phenotypes are conferred by amino acid sequence variations of the FimH adhesins. As few as one amino acid substitution can completely change the substrate specificity of a given FimH adhesin (Sokurenko et al, 1994).

The present inventors have, instead, adopted the anti-idiotypic approach for developing a UTI-specific FimH vaccine. As the sequence variations of FimH between UTI and fecal isolates are minor, a direct FimH vaccine approach is unlikely to discriminate between the two different isolates. In contrast, monoclonal antibodies that react with FimH antigen determinants of the UTI isolates without cross-reacting with the FimH adhesin of the fecal isolates can be produced. Once obtained, these monoclonal antibodies can be used as immunogens to produce monoclonal anti-idiotypic antibodies whose variable regions (v-region) mimic the FimH adhesin of the UTI isolates. This approach provides two major advantages: (1) it yields an unlimited amount of vaccine; and (2) it avoids the possibility of eliminating intestinal *E. coli* flora.

The anti-idiotypic antibody according to the present invention immunospecifically binds to an idiotype of another antibody, where this idiotype is specific for an epitope of FimH adhesin from uropathogenic Type I-fimbriated *E. coli*, which is not present in FimH adhesin from non-uropathogenic Type I-fimbriated *E. coli*. Thus, the anti-idiotypic antibody or an antigen-binding fragment thereof mimics an epitope unique to FimH adhesin from uropathogenic Type I-fimbriated *E. coli* and acts as a surrogate immunogen for this unique FimH adhesin epitope.

When an immunogenic composition containing an immunizing effective amount of the anti-idiotypic antibody or antigen-binding fragment thereof as an active component is administered to a subject according to the present invention, an effective immune response is induced. An immune response is intended to be a humoral response, i.e., production of antibodies, and/or a cellular/cell-mediated response, such as a T-cell response, including helper and cytotoxic T-cell responses.

The polyclonal or, preferably, monoclonal antibodies of the invention may be produced by methods known in the art. These methods include the immunological method described by (Kohler et al., 1975 and Campbell 1985), where an immortal cell line (typically murine myeloma cells) is fused to lymphocytes (typically splenocytes) from a mammal immunized with a preparation containing a given antigen, and the culture supernatants of the resulting hybridoma cells are screened for antibodies against the antigen, as well as by the recombinant DNA method described by (Huse et al., 1989).

One aspect of the present invention further provides a cell which produces the anti-idiotypic antibody of the invention. This cell may be any cell, including genetically engineered bacterial cells, such as *E. coli* cells containing DNA to produce the antibody, as well as the more typical mammalian cells, such as B cells hybridized with murine myeloma cell lines using standard fusion procedures (Kearney et al, 1981).

To produce the anti-idiotypic monoclonal antibodies of the present invention, one may use any antibody (Ab1) reactive with FimH adhesin from uropathogenic Type I-fimbriated *E. coli* but not with non-uropathogenic Type I-fimbriated *E. coli* as the immunogen, or hybridoma cells producing this antibody. Immunization may be accomplished using standard procedures. The unit dose and immunization regimen depend on the species of mammal immunized, its immune status and factors, including the body weight of the mammal. The immunized mammals are typically bled, and the serum from each blood sample is assayed for particular antibodies using appropriate screening assays.

An immortal cell line (e.g., a myeloma cell line) is derived from the same mammalian species as the lymphocytes. Preferred immortal cell lines are mouse myeloma cell lines that are sensitive to culture medium containing hypoxantine, aminopterin and thymidine ("HAT medium") HAT-sensitive mouse myeloma cells are fused to mouse splenocytes using polyethylene glycol (e.g., PEG 3350) (Lerner, 1981). Hybridoma cells resulting from the fusion are then selected using HAT medium, which kills unfused and unproductively fused myeloma cells (unfused splenocytes die after several days because they are not transformed). Hybridomas producing a desired antibody are detected by screening the hybridoma culture supernatants using assays which detect mabs having the desired specificity.

To produce anti-idiotypic antibodies according to the present invention, hybridoma cells that test positive in screening assays are cultured in a nutrient medium under conditions and for a time sufficient to allow the hybridoma cells to secrete the monoclonal antibodies into the culture medium. Tissue culture techniques and culture media suitable for hybridoma cells are well known. The conditioned hybridoma culture supernatant may be collected, and the antibodies optionally further purified by conventional methods.

Alternatively, the desired antibody may be produced by injecting the hybridoma cells into the peritoneal cavity of a mouse primed with 2,6,10,14-tetramethylpentadecane (PRISTANE, Sigma Chemical Co., St. Louis, Mo.). The hybridoma cells proliferate in the peritoneal cavity, secreting the antibody which accumulates as ascites fluid. The antibody may be harvested by withdrawing the ascites fluid from the peritoneal cavity with a syringe.

The term "antibody" as used herein is intended to mean an intact immunoglobulin molecule which includes two each of the immunoglobulin light and heavy chains. Accordingly, antibodies include intact immunoglobulins of types IgA, IgG, IgE, IgD and IgM (as well as subtypes thereof), where the light chains of the immunoglobulin may be of types kappa or lambda. Antibodies also include monoclonal, as well as polyclonal antibodies, recombinant antibodies, humanized recombinant antibodies, and chimeric recombinant antibodies.

As used herein, monoclonal antibodies are monospecific antibodies produced initially by a single clone of antibody forming cells. Recombinant antibodies are antibodies produced by a cell transformed with DNA encoding the light and heavy chains of a given immunoglobulin molecule. Within the antibodies produced recombinantly, "humanized" recombinant antibodies are antibodies initially derived from a non-human mammal in which recombinant DNA technology has been used to substitute some or all of the amino acids from corresponding regions of a human immunoglobulin light or heavy chain. "Chimeric" recombinant antibodies are antibodies derived initially from a non-human mammal in which recombinant DNA technology has been used to replace all or part of the hinge and constant regions of the heavy chain and/or the constant region of the light chain, with corresponding regions from a human immunoglobulin light chain or heavy chain. Suitable non-human mammals include any mammal from which monoclonal antibodies can be made, such as rabbit, rat, mouse, horse, goat, primate, etc.

Recombinant antibodies may be produced using conventional recombinant DNA technique, e.g., by transforming a host cell with a suitable expression vector comprising DNA encoding the light and heavy immunoglobulin chains of a desired antibody. In addition, it is possible to produce recombinant chimeric antibodies, wherein some or all of the hinge and constant regions of the heavy chain and/or the constant region of the light chains of an antibody of this invention have been substituted with corresponding regions of an immunoglobulin light or heavy chain of a different species, and recombinant "humanized" antibodies prepared by CDR grafting, in which all but the complementarity determining region(s) of an antibody are replaced by corresponding parts of a human antibody, to reduce the antigenicity of the antibody (Jones et al, 1986 and Ward et al, U.S. Pat. No. 4,816,397).

In one method of humanization of an animal monoclonal anti-idiotypic antibody, RPAS is combined with the CDR grafting method described by (Daugherty et al., 1991). Briefly, the variable region of DNA of a selected animal recombinant anti-idiotypic single-chain Fv fragment (ScFv) is sequenced by the method of (Clackson et al., 1991). Using this sequence, animal CDRs are distinguished from animal framework regions (FR) based on locations of the CDRs in known sequences of animal variable genes (Kabat et al, 1987). Once the animal CDRs and FR are identified, the CDRs are grafted onto human heavy chain variable region framework by the use of synthetic oligonucleotides and polymerase chain reaction (PCR) recombination. Codons for the animal heavy chain CDRs, as well as the available human heavy chain variable region framework, are built in four (each 100 bases long) oligonucleotides. Using PCR, a grafted DNA sequence of 400 bases is formed that encodes for the recombinant animal CDR/human heavy chain FR. General techniques for cloning murine immunoglobulin variable domains are described, for example, by the publications of (Orlandi et al., 1989), which is incorporated by reference in its entirety. Techniques for producing humanized mAbs are described, for example, by (Jones et al., 1986; Riechmann et al., 1988; Verhoeyen et al., 1988; Carter et al., 1992; Sandhu, 1992 and Singer et al., 1993).

The expression of recombinant CDR-grafted immunoglobulin gene is accomplished by its transfection into human 293 cells (transformed primary embryonic kidney cells, commercially available form American Type Culture Collection, Rockville, Md. 20852) which secrete fully grafted antibody. (See, e.g., Daugherty et al., 1991). Alternatively, humanized ScFv is expressed on the surface of bacteriophage and produced in *E. coli* as in the Recombinant Phage Antibody System (RPAS) of Pharmacia LKB Biotechnology, Sweden, where antibody variable heavy and light chain genes are separately amplified from the hybridoma mRNA and cloned into an expression vector. The heavy and light chain domains are co-expressed on the same polypeptide chain after joining with a short linker DNA which codes for a flexible peptide. This assembly generates a single-chain Fv fragment (ScFv) which incorporates the complete antigen-binding domain of the antibody.

Using the antigen-driven screening system, the ScFv with binding characteristics equivalent to those of the original monoclonal antibody is selected (see, e.g., McCafferty et al, 1990; Clackson et al, 1991, incorporated herein by reference). The recombinant ScFv includes a considerably smaller number of epitopes than the intact monoclonal antibody, and thereby represents a much weaker immunogenic stimulus when injected into humans. An intravenous injection of ScFv into humans is, therefore, expected to be more efficient and immunologically tolerable in comparison with currently used whole monoclonal antibodies (Norman et al, 1993).

In another embodiment, an antibody of the present invention is a human monoclonal antibody. Such antibodies are obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesis human antibodies specific for human antigens, and the mice can be used to produce human antibody-secreting hybridomas. Methods for obtaining human antibodies from transgenic mice are described by (Green et al., 1994; Lonberg et al., 1994; and Taylor et al., 1994).

Furthermore, the present invention includes antigen binding fragments of the antibodies described herein, such as Fab, Fab', F(ab)$_2$, and Fv fragments, fragments comprised of one or more CDRs, single-chain antibodies, heavy chain monomers or dimers, light chain monomers or dimers, and dimers consisting of one heavy chain and one light chain. Such antibody fragments may be produced by chemical methods, e.g., by cleaving an intact antibody with a protease, such as pepsin or papain, or via recombinant DNA techniques, e.g., by using host cells transformed with truncated heavy and/or light chain genes. Synthetic methods of generating such fragments are also contemplated. Heavy and light chain monomers may similarly be produced by treating an intact antibody with a reducing agent, such as dithiothreitol or β-mercaptoethanol, or by using host cells transformed with DNA encoding either the desired heavy chain or light chain or both.

Antibody fragments, which can be produced by enzymatic cleavage of antibodies with pepsin to provide a 5S fragment denoted F(ab')$_2$, can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab fragments with an Fc fragment directly. These methods are described, for example by U.S. Pat. Nos. 4,036,945 and 4,331,647 and references contained therein. (Also, see Nisonoff et al., 1960; Porter, 1959; Edelman et al., 1967 and Coligan, 1991).

Other methods of cleaving antibodies, such as separation of heavy chains to form monovalent light-heavy chain fragments, further cleavage of fragments, or other enzymatic, chemical or genetic techniques may also be used, as long as the fragments bind to the antigen that is recognized by the intact antibody. For example, Fv fragments comprise an association of $V_H$ and $V_L$ chains. This association can be non-covalent, as described in Inbar (1972). Alternatively, the variable chains can be linked by an intermolecular disulfide bond or cross-linked by chemicals, such as glutaraldehyde (see, e.g., Sandhu, 1992).

Preferably, the Fv fragments comprise $V_H$ and $V_L$ chains which are connected by a peptide linker. These single-chain antigen binding proteins (sFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing sFvs are described, for example by (Whitlow, 1991; Bird et al., 1988; Pack et al., 1993; Sandhu, 1992 and U.S. Pat. No. 4,946,778.

Another form of an antibody fragment is a peptide coding for a single CDR. CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (Larrick et al., 1991).

The anti-idiotypic monoclonal antibodies of the present invention are obtained by processes where cells of a hybridoma cell line secreting the desired anti-idiotypic monoclonal antibodies are multiplied in vitro or in vivo. Multiplication in vitro is carried out in suitable culture media, which are the customary standard culture media, such as Dulbecco's Modified Eagle Medium (DMEM) or RPMI 1640 medium, optionally replenished by a mammalian serum, e.g., fetal calf-serum, or trace elements and growth sustaining supplements, e.g., feeder cells such as normal mouse peritoneal exudate cells, spleen cells, bone marrow macrophages, 2-aminoethanol, insulin, transferrin, low density lipoprotein, oleic acid, or the like.

In vitro production provides relatively pure antibody preparations and allows scale-up to give large amounts of the desired antibodies. Techniques for mammalian cell cultivation under tissue culture conditions are known in the art and include homogeneous suspension culture, e.g., in an airlift reactor or in a continuous stirrer reactor, or immobilized or entrapped cell culture, e.g., in hollow fibers, microcapsules, on agarose microbeads or ceramic cartridges.

Large quantities of the desired anti-idiotypic monoclonal antibodies can also be obtained by multiplying the cells in vivo. For this purpose, hybridoma cells producing the desired antibodies are injected into histocompatible mammals to cause growth of antibody-producing tumors. Optionally, the animals are primed with a hydrocarbon, especially mineral oils such as pristane (tetramethylpentadecane), prior to the injection. After one to three weeks, the antibodies are isolated from the body fluids of those mammals. For example, hybridoma cells derived from BALB/c mice that produce the desired monoclonal antibodies are injected intraperitoneally into BALB/c mice optionally pre-treated with pristane, and, after one to two weeks, ascitic fluid is taken from the animals.

The anti-idiotypic antibody and antigen-binding fragments thereof can be used in an immunizing composition according to the present invention by conjugating the antibodies or fragments to a soluble immunogenic carrier protein. The antibody or fragment thereof and the carrier protein are physically associated by a linking means that does not interfere with the ability of either of the linked groups to function as described. Because immunogenic carriers are typically proteins themselves, the techniques of protein conjugation or coupling through activated functional groups is particularly applicable. For a review of those techniques, see Aurameas et al (1978). See also U.S. Pat. Nos. 4,493,795 and 4,671,958.

Useful immunogenic carriers are well known in the art and are generally large proteins. Non-limiting examples of such carriers are keyhold limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acids such as poly (D-lysine: D-glutamic acid), and the like.

The choice of carrier is more dependent upon the ultimate use of the inoculum and is based upon criteria not particularly involved in the present invention. For example, a carrier that does not generate an untoward reaction in the particular mammal to be inoculated should be selected.

A preferred immunizing composition comprises an antibody conjugate or fragment conjugate, and an adjuvant. Examples of suitable adjuvants include aluminum hydroxide and lipid. Methods of formulating vaccine compositions are well-known to those of ordinary skill in the art. (See, for example, Rola 1990).

The preferred pharmaceutical compositions, i.e., immunizing compositions, of the present invention are similar to those used for passive immunization of humans with other antibodies. Typically, the antibodies of the present invention will be suspended in a sterile saline solution for therapeutic uses. The pharmaceutical compositions may alternatively be formulated to control release of the active ingredients or to prolong their presence in a patient's system. Numerous suitable drug delivery systems are known and include, e.g., implantable drug release systems, hydrogels, hydroxymethylcellulose, microcapsules, liposomes, microemulsions, microspheres, and the like. Controlled release preparations can be prepared through the use of polymers to complex or adsorb the antibodies or fragments. For example, biocompatible polymers include matrices of poly(ethylene-co-vinyl acetate) and matrices of a polyanhydride copolymer of a stearic acid dimer and sebaric acid (Sherwood et al, 1992). The rate of release of an antibody or antibody fragment from such a matrix depends upon the molecular weight of the antibody or fragment, the amount of antibody or fragment within the matrix, and the size of dispersed particles (Saltzman et al., 1989 and Sherwood et al., 1992). Other solid dosage forms are described in (Ansel et al., 1990 and Gennaro, 1990).

The pharmaceutical compositions of this invention may be administered by any suitable means, such as orally, intranasally, subcutaneously, intramuscularly, intravenously, intra-arterially, or parenterally. Ordinarily, intravenous (i.v.) or parenteral administration will be preferred.

It will be apparent to those of ordinary skill in the art that the immunizing or immunoprophylactically effective amount of an antibody or an antigen-binding fragment thereof according to the present invention will depend, inter alia upon the administration schedule, the unit dose of antibody or fragment administered, whether the antibody or fragment is administered in combination with other therapeutic agents, the immune status and health of the patient, the therapeutic activity of the antibody or antibody fragment administered and the judgment of the treating physician.

The anti-idiotypic antibody or antigen-binding fragment thereof as the active immunogenic ingredient is dissolved, dispersed or admixed in an excipient that is pharmaceutically acceptable and compatible with the active ingredient as is well known. Suitable excipients are, for example, water, saline, phosphate buffered saline (PBS), dextrose, glycerol, ethanol, or the like and combinations thereof. Other suitable carriers are well-known to those in the art. (See, for example, Ansel et al., 1990 and Gennaro, 1990). In addition, if desired, the immunizing composition can contain minor amounts of auxiliary substances such as wetting or emulsifying agents, pH buffering agents or adjuvants which enhance the effectiveness of the immunizing composition.

The anti-idiotypic monoclonal antibodies (Mabs) according to the invention can also be used for the qualitative and quantitative determination of antibodies directed specifically against FimH from uropathogenic antigen. This is especially useful for the monitoring the efficacy of immunization with the anti-idiotypic Mabs of the present invention.

For instance, the anti-idiotypic monoclonal antibodies according to the invention can be used in any of the known immunoassays which rely on the binding interaction between the idiotopes of the antibodies directed specifically against FimH from uropathogenic E. coli and of the anti-idiotypic monoclonal antibodies. Example of such assays are radio-, enzyme, fluorescence, chemiluminescence, immunoprecipitiation, latex agglutination, and hemagglutionation immunoassays.

The anti-idiotypic monoclonal antibodies according to the invention can be used as such or in the form of radioactively labelled derivatives in a radioimmunoassay (RIA). Any of the known modifications of a RIA can be used, for example soluble phase (homogeneous) RIA, solid phase (heterogeneous) RIA, single RIA or double (sandwich) RIA with direct or indirect (competitive) determination of antibodies directed specifically against FimH adhesin from uropathogenic but not from non-uropathogenic E. coli antigen.

An example of such radioimmunoassay is a sandwich RIA in which a suitable carrier, for example the plastic surface of a microtiter plate or of a test tube, e.g. of polystyrene, polypropylene or polyvinylchloride, glass or plastic beads, filter paper, dextran etc. cellulose acetate or nitrocellulose sheets, magnetic particles or the like, is coated with an anti-idiotypic monoclonal antibody of the present invention by simple adsorption or optionally after activation of the carrier, for example with glutaraldehyde or cyanogen bromide. Test solutions containing antibodies directed specifically against FimH adhesin from uropathogenic but not non-uropathogenic E. coli and finally polyclonal antibodies which also react with the anti-FimH antibodies and which are radioactively labelled, e.g. with $^{125}$I, are added. The amount of antibodies directed against FimH adhesin from uropathogenic but not non-uropathogenic E. coli in the test solution is directly proportional to the amount of bound polyclonal antibodies and is determined by measuring the radioactivity of the solid phase.

The anti-idiotypic monoclonal antibodies according to the invention can be used as such or in the form of enzyme-conjugated derivatives in an enzyme immunoassay. As described above for radioimmunoassays, any of the known modifications of an enzyme immunoassay can be used. The tests are carried out in an analogous manner to the radioimmunoassays described above using an enzyme label instead of a radioactive label. The amount of immune complex formed which corresponds to the amount of antibodies specifically directed against FimH adhesin from uropathogenic but not non-uropathogenic E. coli present in the test solutions is determined by adding an enzyme substrate solution. The enzyme substrate reaction results, for example, in a color change which can be observed by eye or with optical measuring devices.

The anti-idiotypic monoclonal antibodies according to the present invention can be used as such or in the form of derivatives conjugated with chemiluminescent markers in a chemiluminescence immunoassay. As described above for radioimmunoassays, and of the known modifications of a chemiluminescence immunoassay can be used.

The tests are carried out in an analogous manner to the radioimmunoassays described above using a chemiluminescent label instead of a radioactive label. The amount of immune complex formed which corresponds to the amount of antibodies directed against FimH adhesin from uropathogenic but not non-uropathogenic E. coli present in the test solutions is determined by adding a compound tiggering luminescence, e.g. $H_2O_2$ and NaOH, and measuring the emission of light with optical measuring devices.

The use according to the invention of anti-idiotypic monoclonal antibodies and derivatives thereof as described hereinbefore for the determination of antibodies directed against FimH adhesin from uropathogenic but not non-uropathogenic E. coli also includes other immunoassays known per se, for example immunofluorescence assays, latex agglutination, hemagglutination, evanescent light assays using an optical fibre coated with an antiidiotypic Mab and other direct-acting immunosensors which convert the binding event into an electrical or optical signal, or the like.

Suitable labels may be radioactive, enzymatic, fluorescent, magnetic or chemiluminescent. Radiolabeled antibodies are prepared in known ways by coupling a radioactive isotope such as $^3H$, $^{32}p$, $^{35}S$, $^{59}Fe$ $^{125}I$, which can then be detected by gamma counter, scintillation counter or by autoradiography. Anti-idiotypic antibodies of this invention may be suitably labeled with enzymes such as yeast alcohol dehydrogenase, horseradish peroxidase, alkaline phosphatase, and the like, then developed and detected spectrophotometrically or visually. Suitable fluorescent labels include fluorescein isothiocyanate, fluorescamine, rhodamine, and the like. Suitable chemiluminescent labels include luminol, imidazole, oxalate ester, luciferin, and the like.

The present invention also relates to test kits for the qualitative and quantitative determination of antibodies directed against FimH adhesin from uropathogenic but not non-uropathogenic *E. coli* which includes anti-idiotypic monoclonal antibodies of the present invention and/or derivatives thereof and, optionally, other polyclonal or monoclonal antibodies and/or adjuncts.

Test kits according to the present invention for a radioimmunoassay contain, for example, a suitable carrier, optionally freeze-dried solutions of one or more polyclonal and/or monoclonal antibodies, solutions of antibodies directed against buffer solutions, and, optionally, polypeptides or detergents for preventing non-specific adsorption and aggregate formation, pipettes, reaction vessels, calibration curves, instruction manuals and the like. One of the antibodies of the test kit is an anti-idiotypic monoclonal antibody of the present invention.

Having now fully described this invention, it will be appreciated that by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional method steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Abraham et al, "Identification of two ancillary subunits of *Escherichia coli* type 1 fimbriae by using antibodies against synthetic oligopeptides of fim gene products", *J. Bacteriol.* 169:5530–5556 (1987)

Abraham et al, "Conservation of the D-mannose-adhesion protein among type 1 fimbriated members of the family Enterobacteriaceae", *Nature* 336:682–684 (1988)

Ansel et al, *Pharmaceutical Dosage Forms and Drug Delivery Systems,* 5th Ed. (Lea & Febiger 1990)

Aurameas et al, *Scand. J. Immunol.* 8(Supp-1):7–23 (1978)

Bird et al, *Science* 242:423–426 (1988)

Brinton, "The structure, function, synthesis and genetic control of bacterial pili and a molecular model for DNA and RNA transport in gram negative bacter", *Trans. N.Y. Acad. Sci.* 27:1003–1005 (1965)

Campbell in *Laboratory Techniques in Biochemistry and Molecular Biology*, Vol. 13, Burdon et al, Eds., Elsevier Science Publishers (Amsterdam, 1985)

Carter et al, *Proc. Natl. Acad. Sci. USA* 89:4285 (1992)

Clackson et al, "Making antibody fragments using phage display libraries", *Nature* 352:624–688 (1991)

Coligan et al (eds.), *Current Protocols in Immunology*, John Wiley & Sons (1991)

Dalgleish et al, *Vaccine* 6:215–220 (1988)

Daugherty et al, "Polymerase chain reaction facilitates the cloning, CDR-grafting, and rapid expression of a murine monoclonal antibody directed against the CD18 component of leukocyte integrins", *Nucl. Acids Res.* 19:2471–2476 (1991)

Edelman et al, in *Methods in Enzymology*, Vol. 1, Academic Press 1967), p. 422

Eichmann et al, "Idiotypic vaccinations: consideration towards a practical application", *Crit. Rev. Immunol.* 7:93–227 (1987)

Gennaro (ed.), *Remington's Pharmaceutical Sciences,* 18th Ed. (Mack Publishing Company, 1990)

Green et al, *Nature Genet.* 7:13 (1994)

Huse et al, "Generation of a large combinatorial library of the immunoglobulin repertoire in phage lambda", *Science* 246:1275–1281 (1989)

Inbar et al, "Localization of antibody-combining sites within the variable portions of heavy and light chains", *Proc. Natl. Acad. Sci. (USA)* 69:2659 (1972)

Hiernaux, "Idiotypic vaccines and infectious diseases", *Infect. Immun.* 56:1407–1413 (1988)

Jerne, N. K., "Towards a network theory of the immune system", *Ann. Inst. Pasteur. Immun.* 125C:373–389 (1974)

Jones et al, "*Nature* 321:522–525 (1986)

Jones et al, *Proc. Natl. Acad. Sci. USA* 92:2081–2085 (1995)

Kabat et al, *Sequences of Proteinis of Immunological Interest,* 4th Ed., U.S. Health and Human Serivces (Bethesda, Md., 1987)

Kearney et al, "Monoclonal vs. heterogeneous anti-H-8 antibodies in the analysis of the anti-phosphorylcholine response in BALB/c mice", *Eur. J. Immunol.* 11:877 (1981)

Kennedy et al, "Immune response to hepatitis B surface antigen: enhancement by prior injection of antibodies to the idiotype", *Science* 221:853–854 (1983)

Kennedy et al, "Anti-idiotypic antibody vaccine for type B viral hepatitis in chimpanzees", *Science* 232:220–223 (1986)

Kohler et al, "Continuous cultures of fused cells secreting antibody of predefined specificity", *Nature* 256:495–497 (1975)

Langermann et al, "Prevention of mucosal *Escherichia coli* infection by FimH-adhesin-based systemic vaccination", *Science* 276:607–611 (1997)

Larrick et al, *A Companion to Methods in Enzymoloay* 2:106 (1991)

Lerner, R.A., "How to make a hybridoma", *J. Biol. Med.* 54:387–402 (1981)

Lonberg et al, "Antigen-specific human antibodies from mice comprising four distinct genetic modifications", *Nature* 368:856 (1994)

Maurer et al, "Identification and characterization of genes determining receptor binding and pilus length of *Escherichia coli* type 1 pili", *J. Bacteriol.* 169:640–645 (1987)

McCafferty et al, "Phage antibodies: filamentous phage displaying antibody variable domains", *Nature* 348:552–554 (1990)

McNamara et al, *J. Immunol.* 139:2775–2780 (1984)

Nisonoff et al, *Arch. Biochem. Biophys.* 89:230 (1960)

Nisonoff et al, *Clin. Immunol. Immunopathol.* 21:397–406 (1981)

Norman et al, *Transplant Proc.* 25, suppl. 1:89–93 (1993)

Ofek et al, "Adherence of *Escherichia coli* to human mucosal cells mediated by mannose receptors", *Nature* 265:623–625 (1977)

Orlandi et al, "Cloning immunoglobulin variable domains for expression by the polymerase chain reaction", *Proc. Natl. Acad. Sci. (USA)* 86:3833 (1989)

Pack et al, "Improved bivalent miniantibodies, with identical avidity as whole antibodies, produced by high cell density fermentation of *Escherichia coli*", *Bio/Technology* 11:1271–1277 (1993)

Porter, *Biochem. J.* 73:119 (1959)

Poskitt et al, "Internal image (Ab2 beta) anti-idiotype vaccines. Theoretical and practical aspects", *Vaccine* 9:792–796 (1991)

Riechmann et al., "Reshaping human antibodies for therapy", *Nature* 332:323 (1988)

Reid, G., "Effect on uropathogens of prophylaxis for urinary tract infection in spinal cord injured patients: preliminary study", *Spinal Cord* 35:605–607 (1997)

Roitt, *Immunol. Today* 6:265–267 (1985)

Rola, in *Remington's Pharmaceutical Sciences*, 18th Ed. (Gennaro, Ed.) (Mack Publishing Company, 1990)

Russel et al, *J. Bacteriol.* 174:5923–5935 (1992)

Saltzman et al, "Transport rates of proteins in porous materials with known microgeometry", *Biophys. J.* 55:163 (1989)

Sandhu, "Protein engineering of antibodies", *Crit. Rev. Biotech.* 12:437 (1992)

Schreiber et al, "Anti-idiotype-induced, lipopolysaccharide-specific antibody response to Pseudomonas aeruginosa", *J. Immun.* 144:1023–1029 (1990)

Schreiber et al, "Induction of opsonic antibodies to *Pseudomonas aeruginosa* mucoid exopolysaccharide by an anti-idiotypic monoclonal antibody", *J. Infect. Dis.* 164:507–514 (1991)

Service, R. F., *Science* 276:533 (1997)

Sherwood et al, "Controlled antibody delivery systems", *Bio/Technology* 10:1446 (1992)

Shoenfeld et al, "Anti-idiotypes and their application under autoimmune, neoplastic, and infectious conditions", *Int. Arch. Allergy Immunol.* 105:211–223 (1994)

Singer et al., "Optimal humanization of 1B4, an anti-CD18 murine monoclonal antibody, is achieved by correct choice of human V-region framework sequences", *J. Immun.* 150:2844 (1993)

Sokurenko et al, "FimH family of type 1 fimbrial adhesins: functional heterogeneity due to minor sequence variations among fimH genes", *J. Bacteriol.* 176:748–755 (1994)

Sokurenko et al, "Quantitative differences in adhesiveness of type 1 fimbriated *Escherichia coli* due to structural differences in fimH genes", *J. Bacteriol.* 177:3680–3686 (1995)

Sokurenko et al, "Diversity of the *Escherichia coli* type 1 fimbrial lectin. Differential binding to mannosides and uroepithelial cells", *J. Biol. Chem.* 272:17880–17886 (1997)

Stein et al, "Neonatal administration of idiotype or antiidiotype primes for protection against *Escherichia coli* K13 infection in mice", *J. Exp. Med.* 160:1001–1011 (1984)

Taylor et al, *Int. Immun.* 6:579 (1994)

Verhoeyen et al, "Reshaping human antibodies: grafting an antilysozyme activity", *Science* 239:1534 (1988)

Ward et al, *Nature* 341:544–546

Westerink et al, "Development and characterization of an anti-idiotype antibody to the capsular polysaccharide of *Neisseria meningitidis* serogroup C", *C. Infect. Immun.* 56:1120–1127 (1988)

Whitlow et al, "A Companion to Methods in Enzymology 2:97 (1991)

What is claimed is:

1. A monoclonal anti-idiotypic antibody or antigen-binding fragment thereof which immunospecifically binds to an idiotype of a second antibody, wherein said idiotype of said second antibody specifically binds an epitope of FimH adhesin from uropathogenic Type I-fimbriated *Escherichia coil* which is not present in FimH adhesin from non-uropathogenic Type I-fimbriated *Escherichia coli*.

2. A hybridoma cell which produces a monoclonal anti-idiotypic antibody according claim 1.

3. An immunizing composition for stimulating and enhancing, in a subject to which the composition is administered, production of antibodies, which recognize FimH adhesin of uropathogenic Type I-fimbriated *Escherichia coil* but not FimH adhesin of non-uropathogenic Type I-fimbriated *Escherichia coil*, comprising an immunizing effective amount of a monoclonal anti-idiotypic antibody or antigen-binding fragment thereof according to claim 1, and a pharmaceutically acceptable diluent, excipient, carrier or auxiliary agent.

4. A method for stimulating and enhancing production of antibodies, which recognize FimH adhesin of uropathogenic Type I-fimbriated *Escherichia coli* but not FimH adhesin of non-uropathogenic *Escherichia coli*, comprising administering the immunizing composition according to claim 3 to a subject.

* * * * *